United States Patent [19]
Monnet et al.

[11] Patent Number: 5,151,599
[45] Date of Patent: Sep. 29, 1992

[54] DEVICE TO DISPLAY DISINTEGRATIONS OF POSITRONS USING BARYCENTRIC AND TIME OF FLIGHT MEASUREMENTS

[75] Inventors: Olivier Monnet, Moirans; Jacques Vacher, Seyssinet, both of France

[73] Assignee: Commissariat a l'Energie Atomique, Paris, France

[21] Appl. No.: 665,551

[22] Filed: Mar. 5, 1991

[30] Foreign Application Priority Data

Mar. 12, 1990 [FR] France ................ 90 03101

[51] Int. Cl.⁵ .............................. G01T 1/164
[52] U.S. Cl. ................... 250/363.03; 250/363.02; 250/363.01
[58] Field of Search ............ 250/363.03, 363.02, 250/363.01

[56] References Cited

U.S. PATENT DOCUMENTS

| | | | |
|---|---|---|---|
| 4,150,292 | 4/1979 | Ter-Pogossian | 250/363.03 |
| 4,755,680 | 4/1979 | Logan | 250/363.01 |
| 4,864,140 | 9/1989 | Rogers et al. | 250/369 |

OTHER PUBLICATIONS

Ph. Garderet, E. Campagnolo, "Image Reconstruction Using Time of Flight Information in the LETI positron Tomography System," *Workshop on Time-of-Flight Tomography* (Washington University, St. Louis, Mo., May 17–19, 1982) pp. 97–100.

R. Allemand, R. Campagnolo, P. Garderet, R. Gariod, M. Laval, M. Moszynski, E. Tournier, J. Vacher, "Time-of-Flight Method for Positron Tomographic Imaging and State-of-the-Art of Detector Technology for Emission Tomography," *Diagnostic Imaging Medicine PISA* (Italy, Oct. 11–24, 1981).

Primary Examiner—Constantine Hannaher
Attorney, Agent, or Firm—Pearne, Gordon, McCoy & Granger

[57] ABSTRACT

Device to display disintegrations of positrons and comprising at least one pair of scintillators (28) sensitive to gamma radiations and disposed opposite each other, photoelectron multiplier units (30) each associated with one scintillator, devices (34) for the barycentric measurement of the position of scintillations in the scintillators, devices (36) for determining the times of flight of the gamma radiations detected in coincidence in each of the paired scintillators, devices (38) for localizing positron disintegrations, and an image display system (40).

13 Claims, 5 Drawing Sheets

DEVICE TO DISPLAY DISINTEGRATIONS OF POSITRONS USING BARYCENTRIC AND TIME OF FLIGHT MEASUREMENTS

FIELD OF THE INVENTION

The present invention concerns a device to display disintegrations of positrons. The invention can be used in medical applications for studying metabolisms, in pharmacological applications so as to follow up the behavior of a medicine or drug in an organism, and in industrial applications for studying the functioning of parts making use of moving fluids.

BACKGROUND OF THE INVENTION

There already exists a device to display disintegrations of positrons; the positron tomograph which uses the characteristic of the positrons which disintegrate when encountering an electron by emitting two gamma radiations directed alond two opposing directions, each radiation having an energy of 511 keV.

FIG. 1 diagrammatically shows a cutaway view of a positron tomograph.

During a preliminary stage, a substance containing radioactive elements emitting positrons is injected into the organ to be displayed 10 (in this instance, a brain with living tissue, but this organ can be mechanical). The organ 10 is placed at the center of a ring 12 of detectors 14, each formed of a scintillator sensitive to gamma radiations and coupled to a photoelectron multiplier. Each positron emitted disintegrates with one electron after an average free distance covered depending on the organ 10 studied (this average free distance covered is between 2 and 3 mm in thé human body). A disintegration gives rise to an emission of two gamma radiations 11 in opposing directions which are detected in coincidence by the detectors 14 of the ring. These coincidence detections embody an electronic collimation which makes it possible to materialize the track of the coupled gamma radiations.

Next, by means of an image reconstruction treatment using operations such as retroprojections of tracks along several directions, convolutions, etc., it is possible to localize the disintegration points of the positrons.

It can be readily understood that this display is only obtained for one section of the organ 10 situated inside the plane of the ring 12 of the detector 14.

So as to obtain a volume display, several rings 12 are juxtaposed next to one another.

There are known means to improve the sensitivity of positron tomographs by carrying out a complementary measurement, known as a flight measurement, of the gamma radiations which makes it possible to localize each disintegration point of a positon on the corresponding track. The time of flight corresponds to the arrival time difference of two gamma radiations coincidence-detected. A knowledge of the position of the activated detectors 14 obtained by detection of the tracks, the speed of the light and the time of flight makes it possible to localize the emission site of the gamma radiations. In fact, the temporal resolution of the detectors 14 and of the associated analysis electronics only allows for a partial resolution of about 5 cm in the current state of the prior art. The localization obtained by this means is thus not sufficiently precise so as to draw up a cartograph of the disintegration points; it simply makes it possible to restrict the reconstruction range to the track portion situated inside the zone delimited by the time of flight and consequently does not take into account the noise appearing outside this zone. Owing to its inadequate temporal resolution, the time of flight tomograph does not make it possible to dispense with image reconstruction techniques.

Furthermore, in a conventional positron tomograph constituted by one or several rings of discrete detectors, the spatial resolution at the center of the device is roughly equal to the half-width of a detector. Now, a track is separated from its neighboring track by the step between two detectors, which is clearly at least equal to one detector width. The result is that the information received is subsampled. So as to overcome this drawback, the ring or rings is/are driven by an alternating rotary movement with low amplitude enabling each detector to occupy all the intermediate positions between its position at rest and those of its neighboring detectors. This small cicular movement with a radius equal to one half-step between detectors is commonly referred to as "wobbling".

This wobbling required for the sound functioning of positron tomographs results in a significant mechanical complexity rending it difficult to implement the device and proves to be expensive.

There is also another device shown in FIG. 2, called the "gamma camera" known as SPECT (Single Photon Emission Computed Tomograph) allowing for the display of gamma radiations emitted by an organ rendered radio-emitting by injecting a gamma tracer which only produces one gamma radiation per disintegration. There is a description of this SPECT in the patent U.S. Pat. No. 3,011,057. Contrary to the case with positron tomographs which embody an electronic collimation, the SPECTS use a material collimator 16. This collimator is formed by a plate made of an absorbant material, such as lead, pierced with holes orientated either parallel to each other and perpendicular to the surface of the scintillator 18 to which the collimator 16 is attached, or in a direction converging towards the center of the device so as to obtain an enlarging effect. The size and orientation of the holes are such that only the gamma radiations having a corresponding propagation direction are transmitted.

The gamma radiations interacting with the scintillator 18 provoke scintillations which are detected by several photoelectron multiplier tubes 22 disposed side by side on the rear face of the scintillator. The photoelectron multiplier tubes are distanced from the rear face of the scintillator 18 by a film 20 made of a transparent material.

If the scintillator 18 used was in direct contact with the photoelectron multipliers, a scintillation occuring at the center of the detection zone of a photoelectron multiplier and extremely close to the latter could only be detected with difficulty by other photoelectron multipliers without this transparent film 20. Now, it is important that each scintillation is detected by several photoelectron multipliers 22.

In fact, one barycentric measurment of the position of each scintillation is effected by electronic means 24 with the aid of signals proportional to the light intensity detected, these signals being delivered by the photoelectron multiplier tubes 22.

These electronic barycentric measurement means 24 connected to the outputs of the photoelectron multipliers 22 deliver signals indicating the average position of each scintillation on the scintillator 18. This position is solely defined along two directions contained in a plane parallel to the coupling face between the scintillator and the photoelectron multiplier.

So as to obtain a three-dimensional image of the organ, the SPECT rotates around the organ: thus, the directions of the gamma radiations are detected.

All the directions are processed by an image and display reconstruction system (not shown) making it possible to obtain an image of the points emitting a gamma radiation in the organ studied.

Owing to the need to obtain gamma radiations with specific directions before they interact with the scintillator 18, the collimator 16 is required to have holes with an extremely reduced diameter. The quantity of gamma radiations giving rise to scintillations is extremely small. In other words, the sensitivity of a SPECT is slight, which constitutes the major drawback of this type of device. In fact, the lower the sensitivity of the detector is, the stronger needs to be the dose of the radioactive element injected into the organ, this dose being limited when a living organ is to be marked.

In positron tomographs as well as in SPECTS, so as to obtain a three-dimensional image with acceptable resolution, it is necessary to carry out an image reconstruction treatment, which considerably adds to the complexity of the devices.

SUMMARY OF THE INVENTION

One first object of the present invention is to provide a device to display the disintegration of positrons not requiring any image reconstruction treatment so as to obtain an acceptable resolution. Of course, this image reconstruction treatment may be used in the device of the invention so as to improve its resolution.

One second object of the present invention is to provide a sufficiently sensitive device so that the dose of the radioactive element required to mark an organ is small in all cases of use.

One third object of the present invention is to provide a device not requiring any wobbling so as to localize the disintegrations.

In order to do this, the invention recommends the use of at least two scintillators disposed opposite each other and associated with sets of photoelectron multipliers. Coincidence measurements with determination of times of flight are made in correlation with the barycentric position measurements of the scintillations on each of the scintillators.

This information makes it possible to construct a volume image of the positron disintegrations.

More precisely, the invention concerns a device to display positron disintegrations, each disintegration being a source of simultaneous emissions of gamma radiations along two opposing directions, said device comprising:
- at least one pair of scintillators sensitive to gamma radiations and disposed opposite each other, each scintillator having one plurality of faces,
- sets of photoelectron multipliers each associated with one scintillator,
- for each scintillator, an electronic barycentric measuring device connected to the associated photoelectron multiplier unit for measuring the position of the scintillations appearing in the scintillator in question,
- for each pair of scintillators, electronic means connected to the associated sets of photoelectron multipliers for determining the time of flight of gamma radiations detected in coincidence in each of the scintillators of the pair in question,
- an electronic device connected to the barycentric measuring means for localizing disintegrations of positrons and determining times of flight,
- a display system connected to the localization device.

This barycentric measurement makes it possible to localize the position of the tracks of the disintegrations of the positrons inside a plane parallel to the faces opposite the scintillators, whereas the measurement of the time of flight makes it possible to localize the disintegration points on the tracks.

Advantageously, so as to improve the sensitivity of the device of the invention, this device comprises several pairs of opposing scintillators associated with the photoelectron multipliers.

According to one embodiment of the invention, so as to improve the spatial resolution of the device, the latter further includes an image reconstruction system connected to the localization device and including the display system, the device of the invention then comprising several pairs of scintillators or a single pair of scintillators revolving around its axis of symmetry.

The photoelectron multipliers of a unit are distributed on at least one face of the corresponding scintillator.

According to one advantageous embodiment, the photoelectron multipliers of a unit associated with one scintillator are distributed over several faces of this scintillator.

The fact of disposing the photoelectron multipliers on several faces of the scintillators makes it possible to improve the amount of light collected and thus the spatial and temporal resolution (linked to measurement of the time of flight) of the device. In addition, the multiplication of the photoelectron multipliers makes it possible to obtain more accurately the position of the scintillations inside a plane parallel to the opposing faces of the scintillators.

The photoelectron multipliers of one unit associated with one scintillator are preferably distributed over all the faces of this scintillator.

The photoelectron multipliers absorb a slight amount of the 511 keV gamma radiations. Thus, it is possible to dispose them on the face of the scintillators subjected to these radiations so as to improve resolution.

Advantageously, the scintillators are regular prisms with polygonal bases. Of course, other shapes of scintillators may be used, such as cylinders, etc.

The geometry adopted for the scintillators is a geometry which, for a given spatial requirement, makes it possible to dispose the maximum number of photoelectron multipliers on the bases and possibly on the section.

According to one embodiment variant, the scintillators are provided with a device to render uniform their sensitivity to the coincidence gamma radiations.

According to one preferred embodiment of the preceding variant, the device to render uniform the sensitivity of a scintillator is a collimator.

The collimators used in the invention only filter the gamma radiations having a large angle of incidence with the surface of the scintillator, contrary to the case of the collimator of SPECTS which only transits gamma radiations parallel or convergent to a single direction. In fact, the radiations having a large angle of incidence have more changes of having mated radiations emitted in an opposing direction outside the field of the other scintillator of the pair they have created far from the center of the device. Accordingly, the gamma radiations emitted with the large angles of incidence with respect to the surfaces of the scintillators are derived from most of the incidental coincidences detected.

On the other hand, given the fact that the localization of the tracks is effected by coincidence gamma radiations (which corresponds to an electronic collimation), it is pointless to use a material collimator of the type of those collimators used in SPECTS. On the contrary, the use of such a collimator reducing the sensitivity of the device would be extremely disadvantageous.

According to one particular embodiment, the scintillators are $BaF_2$ monolithic crystals.

Equally, it is possible to use any other scintillator crystal ensuring good temporal resolution by virtue of the quality of its scintillation when said crystal is subjected to gamma radiations.

A scintillator crystal may be a monolithic crystal, as well as an association of monolithic crystals optically coupled by optical couplings.

In fact, the scintillators may be mosaic and each may include several crystals able to emit a scintillation light on a scintillation wavelength under the effect of a gamma radiation and having a certain refraction index, these crystals being fixed to one another by an assembling material having a refraction index equal to the refraction index of the crystals and transparent to the scintillation wavelength.

For mosaic scintillators, the crystals are advantageously parallelpiped-shaped and have lateral faces, the crystals being fixed to one another via their lateral faces.

BRIEF DESCRIPTION OF THE DRAWINGS

The characteristics and advantages of the invention shall appear more readily from a reading of the following description, given by way of explanation and being non-restrictive, with reference to the accompanying drawings on which.

DETAILED DESCRIPTION OF THE PREFERRED EMBODIMENTS

Figure 1:
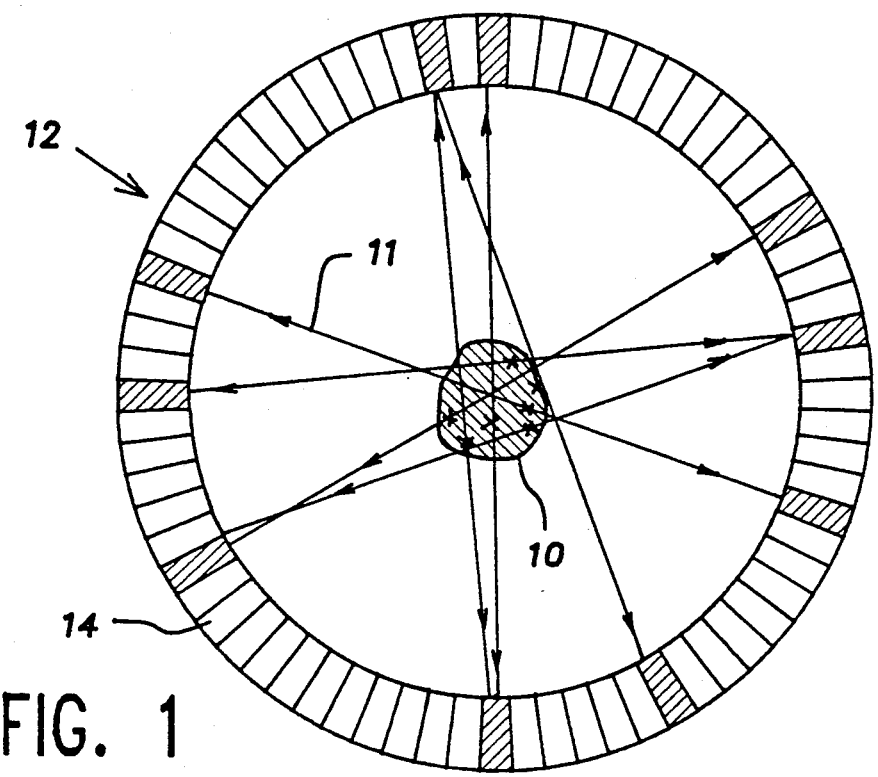
FIG. 1, already described and relating to the prior art, diagrammatically represents a cutaway view of a position tomograph, FIG. 2, already described and relating to the prior art, diagrammatically represents a cutaway view of a SPECT, FIG. 3 diagrammatically represents a partial perspective view of an example of a device conforming to the invention, FIG. 4 diagrammatically represents a device conforming to the invention, FIG. 5 diagrammatically represents one embodiment variant of a device conforming to the invention, FIG. 6 diagrammatically represents a mosaic scintillator.
Figure 2:
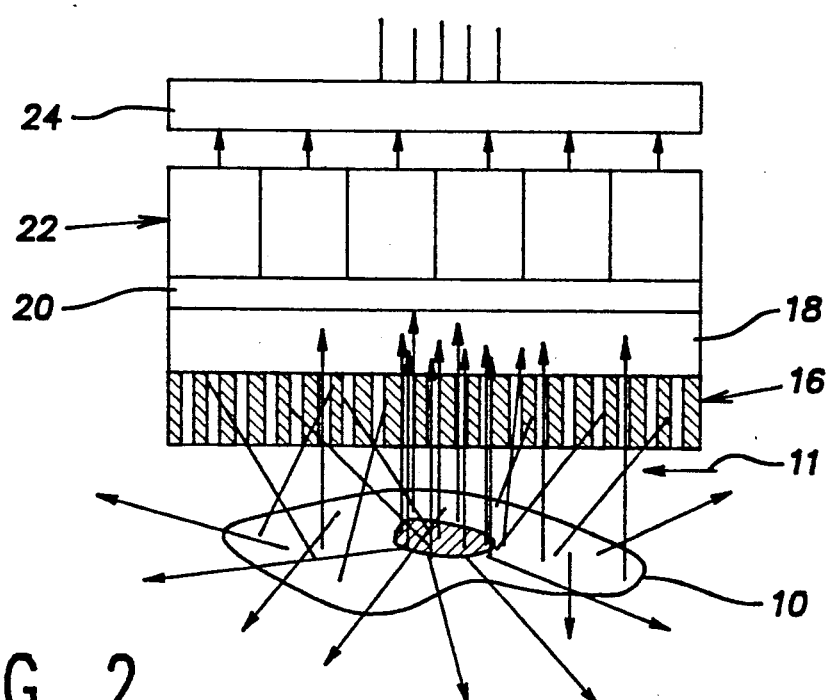
Figure 3:
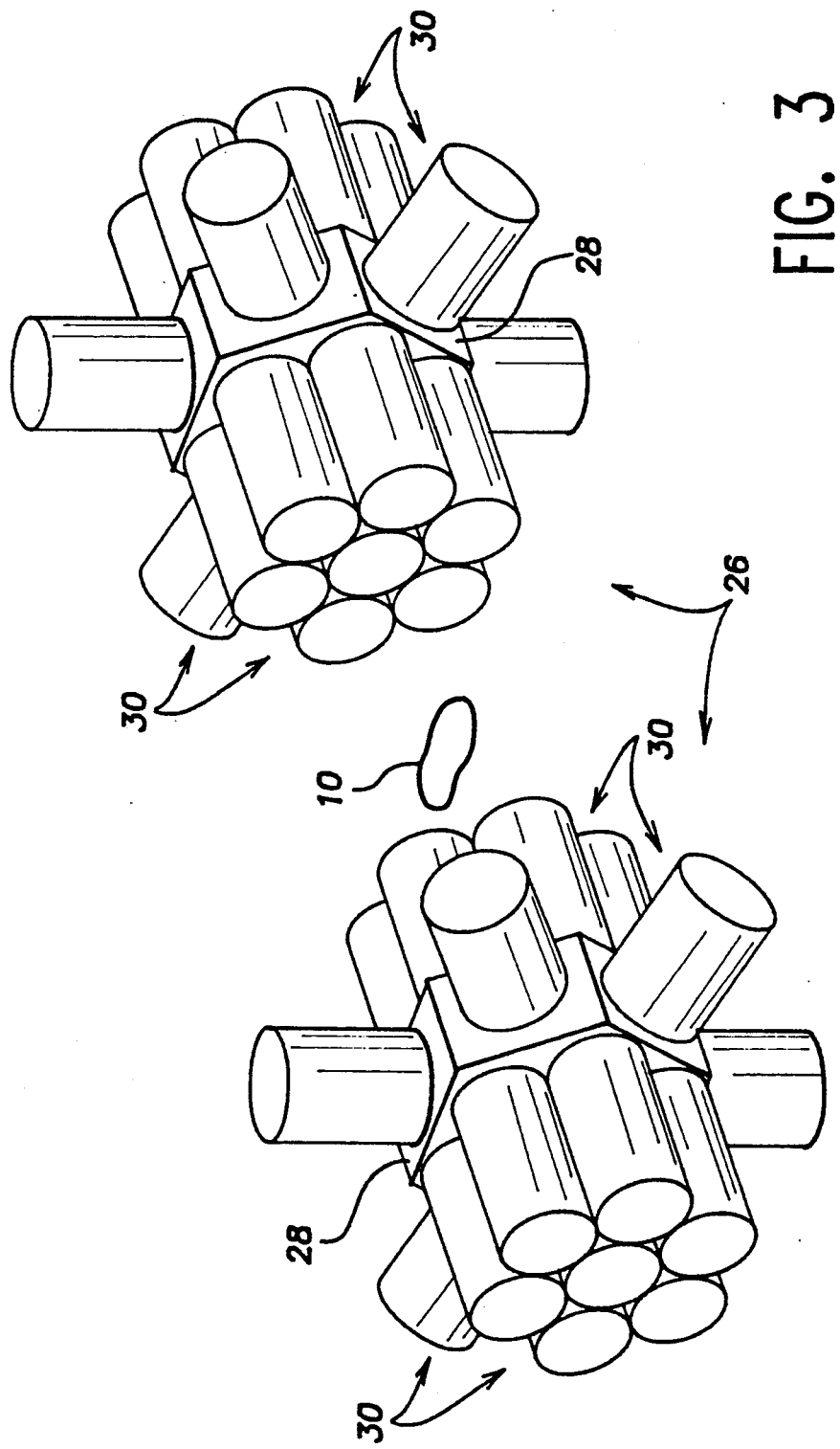

FIG. 3 shows an embodiment of the detectors of a device conforming to the invention. In the example shown, the device comprises a pair of detectors 26 disposed opposite each other. These detectors are disposed on both sides of an organ 10 marked by a radioactive element emitting positions. Each of the detectors 26 comprises a scintillator 28 in the shape of a regular prism with polygonal bases, that is hexagonal in the example shown. The scintillators 28 are $BaF_2$ monolithic crystals having a width between the flat sides of 240 mm for a thickness of 40 mm.

Figure 6:
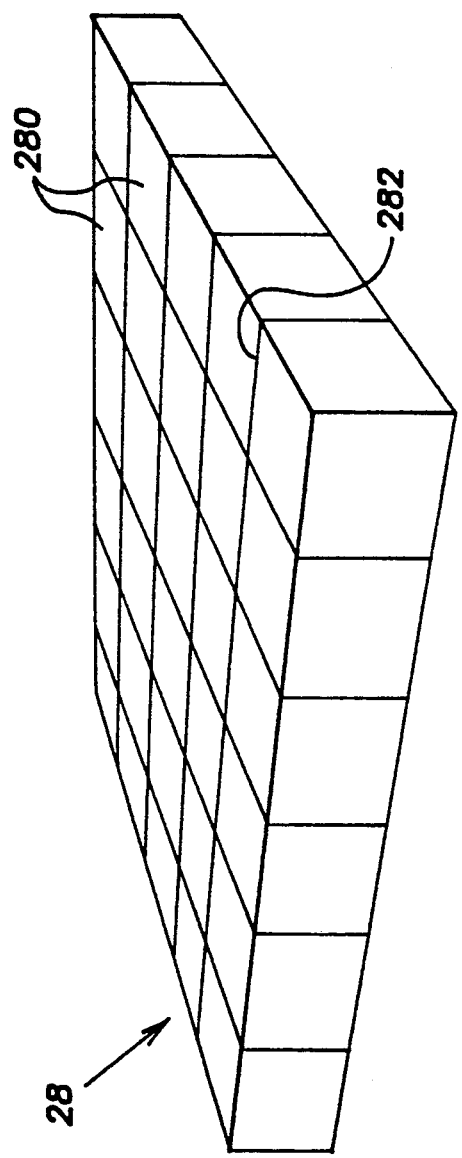

FIG. 6 diagrammatically represents one embodiment variant of a scintillator. In this embodiment example, the scintillator 28 is mosaic: it includes several crystals 280, for example crystals made of $BaF_2$ or CsF, fixed to one another by their lateral faces by means of an assembling material 282.

The assembling material 282 filling up the intervals between the crystals has one refraction index roughly equal to the refraction index of the crystals and is transparent to the scintillation wavelength. This may be a silicon grease, for example of the type commercialized by the Rhône-Poulenc company under the reference 47-V, a cold bonding agent of the type commercialized by the Rhône-Poulenc company or that sold by the Société Générale Electric company under the reference RTV-615, or any other material having the required satisfactory characteristics.

In the example of FIG. 6, the mosaic scintillator 30 comprises parallelpiped crystals 280 with a side length of 50 mm and a thickness of 36 mm so as to constitute a unit with a side length of 25 cm by 30 cm and a thickness of 36 mm.

Each scintillator 28 is associated with one photoelectron multiplier unit 30 able to detect any scintillations due to the interactions of the scintillator in question with the gamma radiations generated by the disintegrations of the positions.

Depending on the crystal used as a scintillator in the invention, a material 20 may be also used between the scintillator and the photoelectron multiplier.

Advantageously, the photoelectron multipliers 30, like the scintillator crystals, have a short response time. Photoelectron multipliers with a short response time are understood to be photomultipliers whose transit time fluctuation of a photoelectron between a photocathode and anode has a standard deviation of less than 0.5 ns, and short response time crystals are understood to be crystals whose width of the luminous pulse is less than several ns ($< \sim 10$ ns). The selected photoelectron multipliers are those of the type referenced XP 2020 Q commercialized by the R.T.C. company.

In the example shown on FIG. 3, each face of the scintillators 28 comprises one or several photoelectron multipliers 30: the bases of the scintillators 28 comprise nineteen juxtaposed photoelectron multipliers 30 (only seven have been shown) and each side face comprises one photoelectron multiplier 30.

As the photomultipliers are transparent to the 511 keV gamma radiations, it is possible to safely place the photomultipliers on the opposing faces of the scintillators 28.

The more photoelectron multipliers there are, the better is the spatial resolution. Secondly, the spatial and temporal resolutions shall be that much better when the light derived from the scintillator is preferably collected by the photoelectron multipliers, (that is, when the overlapping of the scintillator by the photoelectron multipliers shall be optimal). Accordingly, for given scintillator and photoelectron multiplier geometries, the largest possible number of photoelectron multipliers are placed on the various faces of the scintillator.

The detectors 26 are normally provided with lateral "septa", that is, protective plates made of, for example, lead and placed on the sides of the scintillators and intercepting the parasitic gamma radiations derived from sources situated outside the field of the detectors.

The radioactive element extends into the organ 10 and emits positions which by disintegrating emit two gamma radiations of the same energy (511 keV) but in opposing directions. These gamma radiations are emitted in all spatial directions. When a radiation penetrates into a scintillator, it generates a scintillation detected by the photoelectron multipliers. The thickness of the scintillators is such that most of the scintillations are detected by at least two photoelectron multipliers. These photoelectron multipliers deliver a signal proportional to the intensity of the light detected (detected quantity of photons).

An analysis of the coincidences, that is detections carried out by the paired scintillators and an analysis of the times of flight carried out in parallel with determinations of the position of the appearance of scintillations in the scintillators, makes it possible to localize the disintegration points of the positions.

Figure 4:
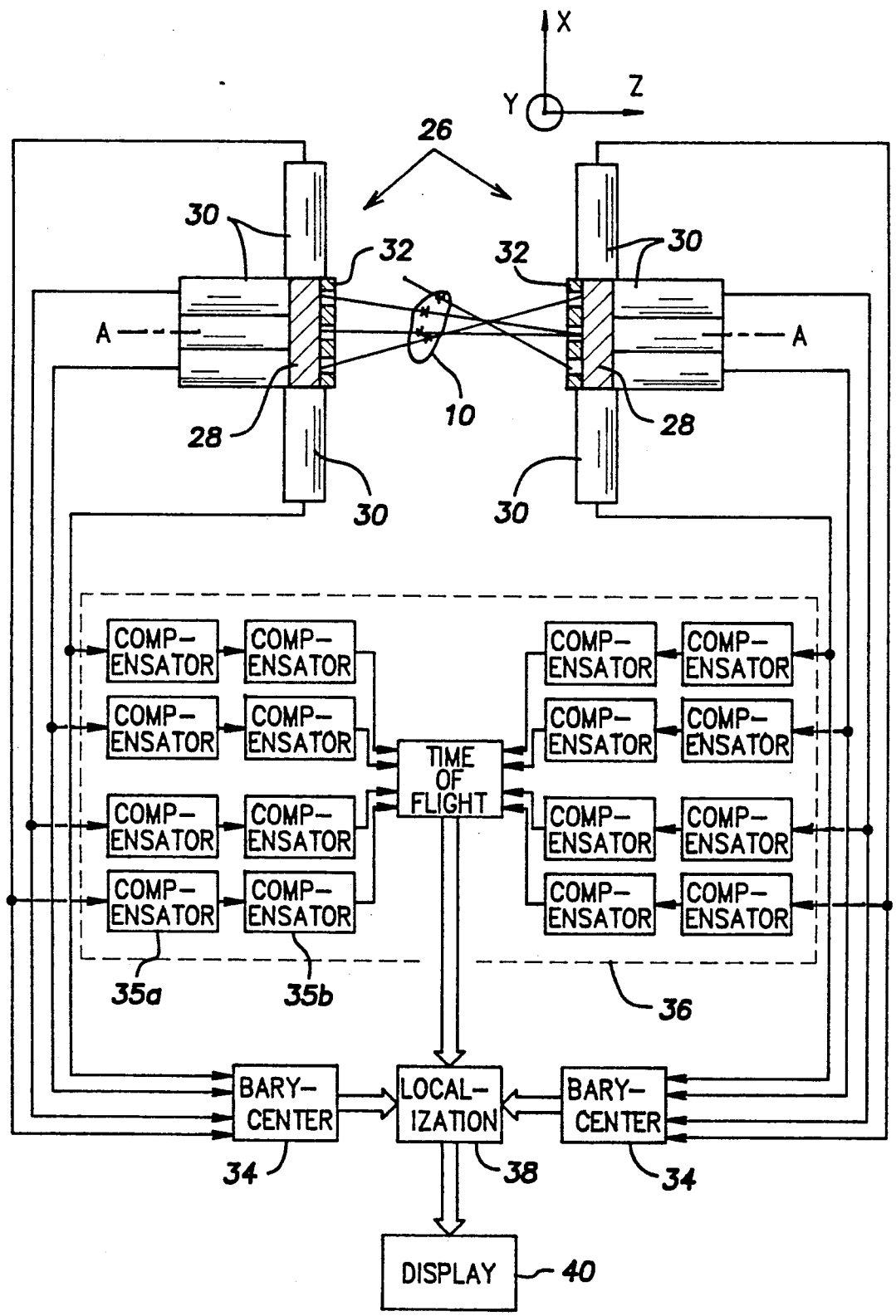

With reference to FIG. 4, this figure shows one embodiment variant of a device conforming to the invention.

In this embodiment, the device comprises a pair of detectors 26 opposite each other shown as a section on the figure. The photoelectron multipliers 30 are disposed on the scintillators 28 identically to the previous embodiment (FIG. 3), except for the fact that the bases opposite the scintillators 28 are deprived of these. On the other hand, these bases comprise a collimator 32 composed of an absorbant material plate made of lead, for example, pierced with holes. If the photoelectron multipliers are coupled onto the internal faces of the crystals (see FIG. 3), the collimator may be placed between these photoelectron multipliers and the organ 10. The collimators 32 have an angle of acceptance of about twenty degrees; this means that the gamma radiations having an incidence greater than half of this angle are intercepted by the absorbant material plate.

This results in a significant reduction of the coincidences derived from radiation source points at the center of the coincidence visual field of the detectors where the angles of incidence may be large. On the other hand, the effect of the collimator is slightly less sensitive for coincidences derived from the edges of the visual field which are derived from the radiations with a small angle of incidence.

As a result, the response of the system is rendered uniform as regards sensitivity between the center and edge of the visual field.

The role of the collimator is also to suppress any single events arriving under a large angle of incidence which improves the fortuitous events/useful events ratio.

Each set of photoelectron multipliers 30 associated with a scintillator 28 is connected to an electronic barycentric device 34 for measuring the position of the scintillations appearing in the scintillator in question. This type of electronic device is described in the patent U.S. Pat. No. 3,011,057 and details shall not be described here in further detail. It merely suffices to say that the scintillations are positioned with respect to an axis X and an axis Y defining a plane parallel to one of the bases of the scintillator in question. These axes X and Y cross at the top of the center of the base of the scintillator. They are each divided into one portion of positive coordinates X+, Y+ and one portion of negative coordinates X−, Y−. The current delivered for each photoelectron multiplier 30 of the unit tranverses four resistors whose values depend on the position of the photomultiplier with the respect to the axes X and Y. The barycenter of the point of the appearance of a scintillation is determined by adding various currents (weighted by the intensity detected by each photoelectron multiplier) derived from the excited photoelectron multipliers.

The barycentric measuring means 34 comprise means for compensating any asynchronism due to the position of the impact point of the gamma radiation on the scintillator 28. In fact, the light-time between its point of creation and each of the photoelectron multipliers depends on localization of the impact point of the gamma radiations.

The barycentric measuring means 34 deliver signals proportional to the position at X and Y of the scintillations appearing in each of the scintillators 28.

In parallel with these barycentric measurements, electronic means 36 for determining the time of flight of the gamma radiations coincidence-detected in each of the scintillators 28 are connected to the two sets of photoelectron multipliers 30. Such means 36 are described in the report entitled "Workshop on time of flight tomography", May 17–19, 1982, Washington University, Saint-Louis, Mo., p. 143–146 and is not described here in further detail. It suffices to state that the signals derived from the photoelectron multipliers 30 associated with each of the scintillators 28 and coicidence-delivered, that is in a determined temporal window, are first of all shaped by a constant fraction discriminator which delivers calibrated pulses. These pulses are input-delivered from an amplitude time converter with an electric signal. This amplitude corresponds to the charge of a constant current capacitor and thus a right linear charge. The charge starts at the arrival of a first pulse and is stopped on the arrival of the next one derived from the coincidence-detected radiation. This amplitude is then converted into a binary value by a digital/analog converter. This value corresponds to the time of flight and is associated with the coordinates X, Y of the corresponding gamma interactions on each scintillator.

The time of flight determination means 36 further include means 35a for processing the signals delivered by the photoelectron multipliers which compensate for the response time differences of the photoelectron multipliers. A prior calibration phase makes it possible to evaluate the individual delay of each photoelectron multiplier.

The means 36 further comprise means 35b for compensating any asynchronism due to the position of the point of impact of the gamma radiation on the scintillator 28.

The addresses of the photoelectron multipliers have already been determined by the means 34 and correspond to the coordinates X and Y.

The signals delivered at the output of the time of flight barycentric measuring and determination means 34 and 36 are applied to the input of an electronic device 38 for localizing the disintegrations of positions which associates the values of the times of flight with the calculated coordinates XY. As the deviation between the scintillators 28 of the pair is known, the data of the positions of the coincidence-detected scintillations and the times of flight make it possible to calculate localization in the relevant space (with respect to a reference mark) of the position disintegration points.

The localization device 38 delivers on one output the coordinates of the disintegration points with respect to the reference mark. This output is connected to a display device 40 which makes it possible to obtain on a screen the various position disintegration densities in the space contained between the two detectors 26. So as to improve the spatial resolution of the device, this display device may be replaced by an image display and reconstruction device. In this particular case, the detectors 26 are animated by a movement of rotation around the axis of symmetry X or Y midway between the detectors 26.

The image reconstruction device is conventionally constituted by means making use of processings, such as projections, retroprojections, convolutions, etc., traditionally used in time of flight tomographs, such as the TTV03 of the D. LETI.

This device is described in the following documents: R. Allemand and al: Diagnostic Imaging Medecine PISA (Italy), Oct. 11-24 1981; Ph. Garderet, E. Campagnolo: Image Reconstruction Using Time of Flight Information in the Leti Position Tomography System—Workshop on Time-of-Flight Tomography, May 19, 1982, St Louis, Mo., p. 97.

Figure 5:
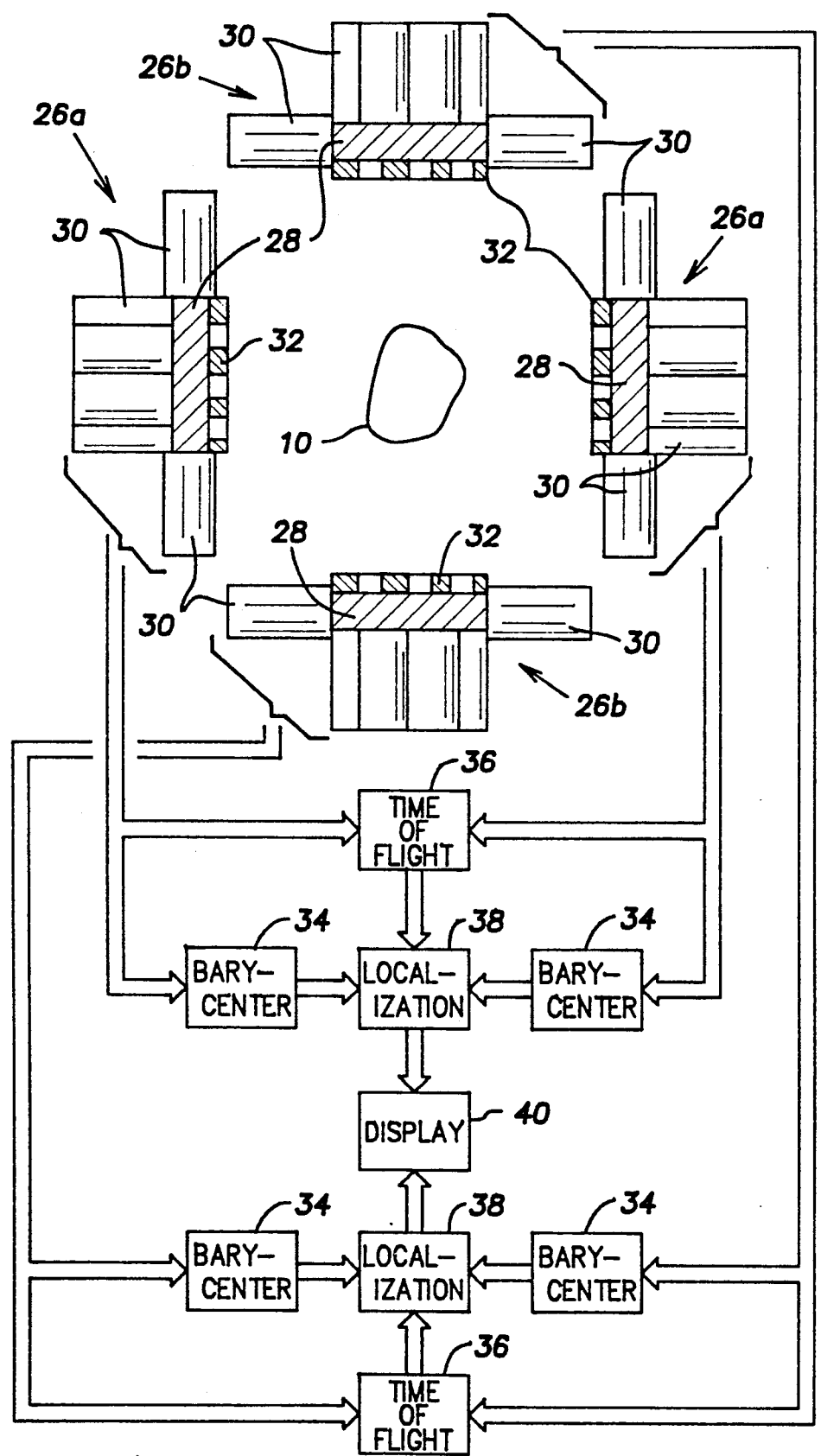

FIG. 5 diagrammatically represents another embodiment variant of a device conforming to the invention. This device comprises two pairs of detectors 26a, 26b. The scintillators 28 of a pair are opposite each other and the two pairs are offset 90° from each other. The electronic barycentric measuring means 34, time of flight means 36 and the disintegration localization means 38 are doubled and each correspond to one pair of detectors.

The display device 40 is connected to the two position disintegration localization means 38, which makes it possible to obtain a device with improved sensitivity.

The display device 40 may be replaced by an image display and reconstruction device, the image reconstruction making it possible to improve spatial resolution, these pairs of detectors possibly being able to rotate around the organ 10.

Of course, a device conforming to the invention is not merely restricted to the embodiment examples described above but covers all possible variants. In particular, it is possible to embody a device conforming to the invention with more than two pairs of scintillators.

What is claimed is:

1. Device to display positron disintegrations, each disintegration being a source of simultaneous emissions of gamma radiations, said device comprising:
   at least one pair of scintillators sensitive to gamma radiations and disposed opposite each other, each scintillator having a plurality of faces,
   sets of photoelectron multipliers each associated with one scintillator,
   for each scintillator, an electronic barycentric measuring device connected to the associated photoelectron multiplier set for measuring the position of the scintillations appearing in the scintillator in question,
   for each pair of scintillators, electronic means connected to the associated sets of photoelectron multipliers for determining the times of flight of gamma radiations coincidence—detected in each of the scintillators of the pair in question,
   an electronic device for localizing the disintegrations of positrons, said localizing device being connected to the electronic barycentric measuring devices and to the means for determining the times of flight and providing a three-dimensional location for the disintegrations, two dimensions being established by the electronic barycentric measuring devices and the third by the means for determining times for flight,
   a display system connected to the localization device for displaying a visual indication in response to said three-dimensional locations.

2. Device according to claim 1 and including several pairs of opposing scintillators associated with the photoelectron multipliers.

3. Device according to claim 1 and further including an image reconstruction system connected to the localization device and including the display system.

4. Device according to claim 3 and including a pair of scintaillators rotating around its center of symmetry.

5. Device according to claim 1, wherein the photoelectron multiplifiers of a set associated with a scintillator are distributed over at least one face of this scintillaror.

6. Device according to claim 5, wherein the photoelectron multiplifiers of a set associated with a scintillator are distributed over all the faces of this scintillator.

7. Device according to claim 1, wherein the scintillators are regular prisms with polygonal bases.

8. Device according to claim 1, wherein the scintillators are provided with a device for rendering uniform their sensitivity to gamma radiations.

9. Device according to claim 8, wherein the device to render uniform the sensitivity of a scintillator is a collimator.

10. Device according to claim 1, wherein the scintilators are $B_aF_2$ monolithic crystals.

11. Device according to claim 1, wherein the scintillators are mosaics and each include several crystals able to emit a scintillation light at a scintillation wavelength under the effect of a gamma radiation and having a certain refraction index, these crystals being fixed to one another by an assembling material having a refraction index roughly equal to the refraction index of the crystals and transparent at the scintillation wavelength.

12. Device according to claim 11, wherein the crystals are parallelpiped-shaped crystals having lateral faces, these crystals being fixed to one another via their lateral faces.

13. A device according to claim 1, wherein the time of flight determination means further include means for compensating any asynchronism due to the position of the point of impact of the gamma radiation on the scintillators.

* * * * *

UNITED STATES PATENT AND TRADEMARK OFFICE
CERTIFICATE OF CORRECTION

PATENT NO. : 5,151,599

DATED : September 29, 1992

INVENTOR(S) : Olivier Monnet and Jacques Vacher

It is certified that error appears in the above-identified patent and that said Letters Patent is hereby corrected as shown below:

On the title page, Item [56]: other Publications, line 2, delete "positron" and insert --Positron--.

Column 1, line 17, delete ";" (semicolon) and insert --:-- (colon); and line 20, delete "alond" and insert --along--.

Column 2, line 25, after "device" insert --,-- (comma).

Column 4, line 65, delete "changes" and insert --chances--.

Column 7, line 67, delete "the" (first occurrence).

Column 10, line 25, delete "multiplifiers" and insert --multipliers--; and line 29, delete "multiplifiers" and insert --multipliers--.

Signed and Sealed this

Twenty-sixth Day of October, 1993

Attest:

BRUCE LEHMAN

*Attesting Officer*     *Commissioner of Patents and Trademarks*